United States Patent [19]

Satoh et al.

[11] Patent Number: 5,399,763

[45] Date of Patent: Mar. 21, 1995

[54] PROCESS FOR PREPARING OPTICALLY ACTIVE 2-AMINOPROPANAL

[75] Inventors: Hisao Satoh, Koshigaya; Taichi Koshigoe, Higashimatsuyama, both of Japan

[73] Assignee: Nippon Kayaku Kabushiki Kaisha, Tokyo, Japan

[21] Appl. No.: 182,285

[22] Filed: Jan. 14, 1994

[30] Foreign Application Priority Data

Feb. 1, 1993 [JP] Japan .................. 5-033965

[51] Int. Cl.$^6$ ............... C07C 223/02; C07C 227/12; C07C 227/04
[52] U.S. Cl. ..................... 564/343; 564/453; 564/454; 564/455; 564/462; 564/468; 564/502; 564/503; 564/506
[58] Field of Search .............. 564/462, 468, 502, 506, 564/453, 454, 455, 503, 343

[56] References Cited

U.S. PATENT DOCUMENTS 4,711,958 12/1987 Iizuka et al. .................. 544/139
5,276,190 1/1994 Boesten et al. .................. 564/30

FOREIGN PATENT DOCUMENTS 62-234071 10/1987 Japan .

OTHER PUBLICATIONS

Journal of Organic Chemistry, 52, 1487–1492 (1987).

*Primary Examiner*—Johann Richter
*Assistant Examiner*—Michael B. Hydorn
*Attorney, Agent, or Firm*—Nields & Lemack

[57] ABSTRACT

A process for preparing an optically active 2-aminopropanal through oxidative cleavage of the corresponding optically active 3-amino-1,2-butanediol of the following formula (2):

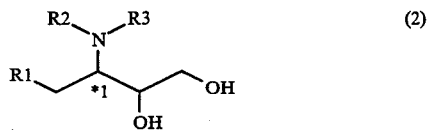

wherein R1 is a hydrocarbon group having 3 to 6 carbon atoms; R2 and R3 are each a hydrogen atom, or separately or together represent an N-protecting group; and the configuration at the *1 position is S or R. An optically active 2-aminopropanal of high purity can be obtained in a high yield by the process.

10 Claims, No Drawings

PROCESS FOR PREPARING OPTICALLY ACTIVE 2-AMINOPROPANAL

BACKGROUND OF THE INVENTION

1. Field of the Invention

The present invention relates to a process for preparing an optically active 2-aminopropanal, which is widely used as a starting material for synthesis of intermediates of drugs, examples of which include an intermediate of bestatin as a carcinostatic, an intermediate of a renin inhibitor as a hypotensor and an intermediate of an HIV protease inhibitor.

2. Description of the Related Art

Two general processes are known for preparing an optically active 2-aminopropanal using an a-amino acid as a starting material. According to one process, an α-amino acid is reduced to the corresponding α-amino alcohol, which is then oxidized to the corresponding aldehyde (see Japanese Patent Laid-Open No. 23,4071/1987). According to another process, an α-amino acid is esterified, and the resulting ester is reduced to the corresponding aldehyde under mild conditions.

In the first-mentioned process comprising reduction of an α-amino acid to the corresponding α-amino alcohol and subsequent oxidation thereof to the corresponding aldehyde, a relatively mild oxidation reaction is carried out from the viewpoint of problems of oxidation to an unstable aldehyde and epimerization thereof. Examples of such a mild oxidation reaction include oxidation with chromium oxide-pyridine and oxidation with dimethyl sulfoxide [see Journal of Organic Chemistry, 52, 1487 (1987)]. Further, oxidation with pyridinium dichromate is known. According to any one of these reactions, however, by-product(s) is formed, while there is a possibility that epimerization of the amino group might occur because the liquid systems involved in the reaction and post-treatments are not always neutral.

On the other hand, in the second-mentioned process comprising esterification of an α-amino acid and subsequent reduction of the resulting ester, a mild reduction reaction is carried out from the viewpoint of reduction to an unstable aldehyde as well. Reduction with diisobutylaluminum hydride may be mentioned as a general mild reduction method (see, for example, Journal of Organic Chemistry, 52, 1487 (1987), wherein an example of synthesis is described).

According to this process as well, however, delicate control of the equivalent number of a reducing agent and a reaction temperature as low as −60° to −78° C. are necessary because reduction of the ester must be terminated just when the aldehyde is formed. Further, this process involves a problem that, even when the equivalent number of the reducing agent is controlled, unreacted matter remains and an alcohol is formed as a result of further reaction. As described hereinabove, an optically active α-amino aldehyde is one of the aldehydes which are difficult to synthesize, because such an aldehyde is unstable in itself and characteristically subject to epimerization of the amino group thereof at the α-position because of the influence thereon of the aldehyde group.

SUMMARY OF THE INVENTION

An object of the present invention is to provide a process for preparing an optically active 2-aminopropanal with the foregoing problems solved.

As a result of intensive investigations with a view to solving the foregoing problems, the inventors of the present invention have completed the present invention.

In accordance with one aspect of the present invention, there is provided a process for preparing an optically active 2-aminopropanal represented by the following general formula (1):

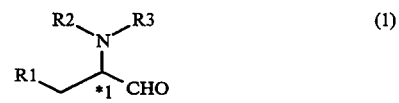  (1)

wherein R1 is a hydrocarbon group having 3 to 6 carbon atoms; R2 and R3 are each a hydrogen atom, or separately or integrally an N-protecting group; and the configuration at the position *1 is S or R:

comprising oxidative cleavage of an optically active 3-amino-1,2-butanediol represented by the following general formula (2):

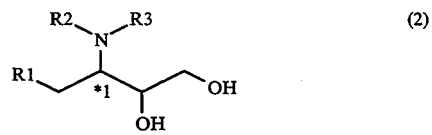  (2)

wherein R1, R2, R3, and the configuration at the position *1 are each as defined above.

In accordance with another aspect of the present invention, there is provided a process for preparing an optically active 2-aminopropanal represented by the following general formula (1):

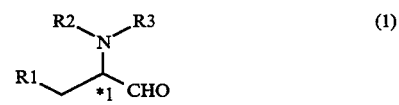  (1)

wherein R1 is a hydrocarbon group having 3 to 6 carbon atoms; R2 and R3 are each a hydrogen atom, or separately or integrally an N-protecting group; and the configuration at the position *1 is S or R:

comprising reduction of an optically active 3-amino-2-hydroxybutyric acid or ester represented by the following general formula (3):

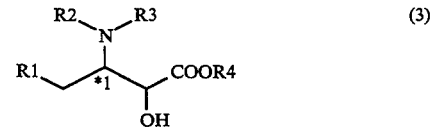  (3)

wherein R1, R2, R3, and the configuration at the position *1 are each as defined above; and R4 is a hydrogen atom or an ester residue; and oxidative cleavage of the resulting optically active 3-amino-1,2-butanediol represented by the following general formula (2):

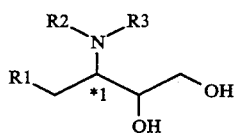

(2)

wherein R1, R2, R3, and the configuration at the position *1 are each as defined above.

DETAILED DESCRIPTION OF THE INVENTION

In the present invention, the compound of the formula (2) can be obtained by reducing to an alcohol group the carboxyl or carboxylate group of an optically active 3-amino-2-hydroxybutyric acid or ester represented by the formula (3):

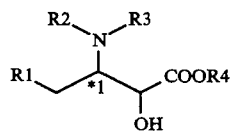

(3)

wherein R1 is a hydrocarbon group having 3 to 6 carbon atoms; R2 and R3 are each a hydrogen atom, or separately or integrally an N-protecting group; R4 is a hydrogen atom or an ester residue; and the configuration at the position *1 is S or R.

In the present invention, the hydrocarbon group having 3 to 6 carbon atoms as R1 in the formula (1) to (3) may be any of saturated and unsaturated cyclic and acyclic groups. Examples of the cyclic hydrocarbon group include phenyl and cyclohexyl groups, while those of the acyclic hydrocarbon group include propyl, butyl and pentyl groups.

All known amino-protecting groups can be used as the N-protecting group which R2 and/or R3 stands for in the formula (1) to (3), and R2 and R3 may be bonded to each other to form a single N-protecting group. Preferred examples of the N-protecting group include acyl type protecting groups such as formyl, acetyl, trifluoroacetyl, and substituted and unsubstituted benzoyl; urethane-forming type protecting groups such as substituted and unsubstituted benzyloxycarbonyl, alkoxycarbonyl with the alkoxy having 1 to 6 carbon atoms, and cycloalkanoxycarbonyl; and other protecting groups including alkoxyalkyl groups such as methoxymethyl, arylalkyl groups such as benzyl and trityl, aryl groups, substituted and unsubstituted arylsulfonyl groups, a phthalyl group, and an o-nitrophenylsulfenyl group. Examples of the ester residue which R4 stands for in the formula (3) include alkyl groups having 1 to 4 carbon atoms, aryl groups, and arylalkyl groups. Specific examples of the alkyl groups having 1 to 4 carbon atoms include methyl, ethyl, propyl, isopropyl, butyl, and isobutyl. Specific examples of the aryl group include phenyl and naphthyl, while those of the arylalkyl group include benzyl. The above-mentioned groups may be substituented.

The reduction of the carboxyl or carboxylate group to the alcohol group to obtain the diol compound of the formula (2) from the butyric acid or ester compound of the formula (3) may be carried out according to any one of customary methods of reducing a carboxyl or carboxylate group to an alcohol group, preferred examples of which include a method wherein use is made of a boron hydride compound or an aluminum hydride compound, a method wherein use is made of diborane, and the Birch reduction method wherein use is made of sodium or lithium. In general, however, the method wherein use is made of a boron hydride compound or an aluminum hydride compound is employed.

In the case where a boron hydride compound is used as a reducing agent, the reactivity thereof is so low that when the reduction reaction is carried out under mild conditions, the reactive group of the compound of the formula (3) must be an ester group, though the N-protecting group is not particularly restricted. Examples of the boron hydride compound to be used in the reaction include sodium borohydride, calcium borohydride, and lithium borohydride. The amount of the boron hydride compound to be used in carrying out the reaction may be 1 to 10 equivalents, preferably 2 to 4 equivalents, based on the reaction substrate. The boron hydride compound may be added either as such in a solid state or in the form of a solution to the reaction system. Alternatively, the boron hydride compound may sometimes be formed in the reaction system and used for the reaction. In the case of sodium borohydride, the reaction is carried out using as a solvent a lower alcohol such as methanol, ethanol or propanol at a temperature of $-20°$ C. to the reflux temperature of the solvent, preferably 10° to 40° C. In the case of calcium borohydride, a solution of calcium chloride may sometimes be added to a solution of sodium borohydride to form, in the reaction system, calcium borohydride, which is then used for the reaction. The solvents of such solutions are preferably the same as the reaction solvent. The reaction solvent, though not particularly restricted, is usually a lower alcohol such as methanol, ethanol or propanol, which may be used in carrying out the reaction at a temperature of $-20°$ C. to room temperature, preferably $-10°$ to 10° C. In the case of lithium borohydride, an ether such as diethyl ether or tetrahydrofuran may be used as a solvent wherein the reaction is carried out at a temperature of room temperature to the reflux temperature of the solvent, preferably the reflux temperature of the solvent, at which the reaction proceeds rapidly. After the completion of the reaction, customary post-treatments may be carried out to obtain the diol compound of the formula (2).

In the case where an aluminum hydride compound is used as a reducing agent, the reactive group of the compound of the formula (3) may be any of the carboxyl and carboxylate groups, though usable examples of the N-protecting group is restricted to arylalkyl groups, alkoxyalkyl groups, aryl groups, arylsulfonyl groups, and the like, which are not reactive with the reducing agent. In this case, specific examples of the N-protecting group include methoxymethyl, benzyl and trityl groups. The amount of the reducing agent to be used in carrying out the reaction may be 1 to 10 equivalents, preferably 2 to 4 equivalents, based on the reaction substrate.

Examples of the aluminum hydride compound include (a) dialkylaluminum hydride compounds with each alkyl group having 3 to 6 carbon atoms, such as diisobutylaluminum hydride; and (b) alkali metal aluminum hydride compounds such as lithium aluminum hydride and sodium aluminum hydride. In the case of the aluminum hydride compound, usable reaction solvents include ethers such as diethyl ether and tetrahydrofuran; aromatic hydrocarbons such as benzene and toluene; and saturated hydrocarbons such as pentane, hexane, and cyclohexane. In this case, the reaction may be carried out at a temperature of 0° to 60° C., preferably 10° to 40° C.

After the completion of the reaction, customary post-treatments may be carried out to obtain the diol compound of the formula (2).

In the case of lithium aluminum hydride, an ether such as diethyl ether or tetrahydrofuran is usually used as the reaction solvent, wherein the reaction may be carried out at a temperature of −10° C. to the reflux temperature of the solvent. In this case, the reaction is preferably carried out at a temperature of 0° C. to room temperature (about 30° C.) where the reactive group of the compound of the formula (3) is an ester group, and at a temperature of 10° C. to the reflux temperature of the solvent where the reactive group of the compound of the formula (3) is a carboxyl group. After the completion of the reaction, customary post-treatments may be carried out to obtain the diol compound of the formula (2).

Examples of the aforementioned sodium aluminum hydride compounds include bis(lower alkoxy or lower alkyl)aluminum hydrides such as sodium bis(2-methoxyethoxy)aluminum hydride and sodium diethylaluminum hydride. In the case where use is made of a sodium aluminum hydride compound, usable reaction solvents include ethers such as diethyl ether and tetrahydrofuran; and aromatic hydrocarbons such as benzene and toluene. In this case, the reaction may be carried out at a temperature of 0° C. to the reflux temperature of the solvent. Somewhat like in the case of lithium aluminum hydride, the reaction is carried out preferably at around room temperature where the reactive group of the compound of the formula (3) is an ester group, and preferably at around the reflux temperature of the solvent (e.g., 60° to 120° C.) where the reactive group of the compound of the formula (3) is a carboxyl group. After the completion of the reaction, customary post-treatments may be carried out to obtain the diol compound of the formula (2).

The oxidative cleavage reaction of the diol compound of the formula (2) thus obtained may be carried out according to a method wherein use is made of a periodic acid compound such as periodic acid or a salt thereof, or a method wherein use is made of lead tetraacetate. The method wherein use is made of a periodic acid compound is preferred from the viewpoint of waste disposal, little formation of by-product(s), etc. Further preferred is a method wherein use is made of a salt of periodic acid, according to which the reaction can be carried out under such neutral conditions as not to cause epimerization, etc.

Preferred examples of the salt of periodic acid that may be used in the reaction include alkali metal periodates such as sodium periodate and potassium periodate. The amount of the salt of periodic acid that may be used in the reaction may be 1 to 5 equivalents, preferably 1 to 3 equivalents. The reaction may be carried out in a solvent mixture mainly composed of water and an organic solvent. Examples of the organic solvent, though not particularly restricted so long as they can dissolve the reaction substrate, include lower alcohols such as methanol, ethanol, and propanol; ethers such as diethyl ether and tetrahydrofuran; aliphatic hydrocarbons such as pentane, hexane, and heptane; lower alkyl halides with each alkyl having 1 to 5 carbon atoms, such as methylene chloride and chloroform; aromatic hydrocarbons such as benzene, toluene, and xylene; and petroleum ether. The reaction temperature may be about −10° C. to around room temperature, preferably −10° to 10° C. at which no side reactions occur. The reaction is preferably carried out under such neutral conditions as not to cause epimerization, etc. After the completion of the reaction, water may further be added to the reaction mixture to dissolve therein inorganic salts, followed by operations of extraction with an extractant, washing, drying and distilling off the extractant to obtain the 2-aminopropanal of the formula (1).

Examples of the ester compound of the formula (3) that may be used as the starting material in the present invention are as follows:

(1) isopropyl (2R,3S)-3-(N-benzyloxycarbonyl)-amino-4-cyclohexyl-2-hydroxybutyrate;

(2) ethyl (2R,3S)-3-(N-benzoyl)-amino-4-phenyl-2-hydroxybutyrate; and (3) isopropyl (2R,3S)-3-(N-butoxycarbonyl)-amino-4-cyclohexyl-2-hydroxybutyrate.

The compound of the formula (3) is obtained according to the method disclosed in Japanese Patent Publication No. 21,466/1986 or a similar method by catalytic reduction of an N-protected threo-3-amino-2-hydroxy-4-oxo-4-hydrocarbyl (having 3 to 6 carbon atoms, such as phenyl or cyclohexyl)butyric acid or ester in the presence of a catalyst such as a palladium catalyst or a Raney nickel catalyst, removal of the amino-protecting group if necessary, and subsequent optical resolution of the resulting product. Alternatively, the compound (3) is obtained by introducing an amino-protecting group into a 2(R)-hydroxy-3-(S)-amino-4-hydrocarbylbutyric acid or ester disclosed in Japanese Patent Laid-Open No. 183,551/1988.

Examples of the diol compound of the formula (2) to be used in the present invention are as follows:

(1) (2R,3S)-3-(N-benzyloxycarbonyl)-amino-4-cyclohexyl-1,2-butanediol;

(2) (2R,3S)-3-(N-benzoyl)-amino-4-phenyl-1,2-butanediol; and (3) (2R,3S)-3-(N-butoxycarbonyl)-amino-4-cyclohexyl-1,2-butanediol.

Examples of the 2-aminopropanal compound of the formula (1) to be obtained according to the present invention are as follows:

(1) 2S-(N-benzyloxycarbonyl)-cyclohexylalaninal;

(2) 2S-(N-benzoyl)-phenylalaninal; and (3) 2S-(N-butoxycarbonyl)-cyclohexylalaninal.

The following Examples will specifically illustrate the present invention, but should not be construed as limiting the scope of the invention.

EXAMPLE 1

(a) (2R,3S)-3-(N-Z)-amino-4-cyclohexyl-1,2-butanediol 216.8 g of isopropyl (2R,3S)-3-(N-Z)-amino-4-cyclohexyl-2-hydroxybutyrate was dissolved in 1,750 ml of ethanol. 86.6 g of sodium borohydride was added to the resulting solution under stirring, and the resulting mixture was cooled to 0° C. A solution of calcium chloride in 857 ml of ethanol was slowly dropped into the cooled mixture. The resulting mixture was stirred for 4 hours. After the completion of the reaction, the reaction mixture was neutralized with 3N HCl to adjust the pH thereof to 5, followed by distilling off the solvent under reduced pressure. Water and ethyl acetate were added to the resulting concentrate to effect extraction. The ethyl acetate layer was washed with an aqueous saturated solution of sodium chloride, dried over sodium sulfate, and filtered. The filtrate was concentrated, and the concentrate was purified by recrystallization to obtain 147.1 g of (2R,3S)-3-(N-Z)-amino-4-cyclohexyl-1,2-butanediol in a yield of 80%.

Here, Z stands for benzyloxycarbonyl.

1H-NMR (CDCl$_3$+D$_2$O)

δ(ppm) 0.72–1.86 (m, 13H) 3.42–3.71 (br, 3H) 3.78–3.95 (br, 1H) 4.86–5.03 (br, 1H) 5.11 (s, 2H) 7.27–7.42 (m, 5H)

Optical rotation [α]20D = −29.53 (cl.002, MeOH)

Melting point: 78.5°–79.5° C.

Here, isopropyl (2R,3S)-3-(N-Z)-amino-4-cyclohexyl-2-hydroxybutyrate as the starting material can be obtained by treating 2-propyl 2(R)-hydroxy-3(S)-amino-4-cyclohexylbutyrate disclosed in Japanese Patent Laid-Open No. 183,551/1988 with benzyl S-4,6-dimethylpyrimidin-2-yl thiolcarbonate, triethylamine, water and dioxane according to substantially the same procedure as the one disclosed in Example 1 (5) of Japanese Patent Publication No. 21,466/1986.

(b) 2S-(N-Z)-cyclohexylanalinal 50 g of (2R,3S)-3-(N-Z)-amino-4-cyclohexyl-1,2-butanediol was added to a solvent mixture composed of 180 ml of ethyl ether and 75 ml of water. The resulting mixture was cooled to 0° C. 49.9 g of sodium periodate was added to the cooled mixture under stirring to effect the reaction for 1 hour. After the completion of the reaction, water was added to the reaction mixture to dissolve therein inorganic salts, followed by extraction with ethyl ether. The ethyl ether layer was washed with water and an aqueous saturated solution of sodium chloride, dried over sodium sulfate, and filtered. The filtrate was then concentrated to quantitatively obtain 44.8 g of S-(N-Z)-cyclohexylalaninal.

1H-NMR (CDCl$_3$)

δ(ppm) 0.75–1.91 (m, 13H) 4.24–4.44 (m, 1H) 5.12 (s, 2H) 5.14–5.29 (m, 1H) 7.26–7.44 (m, 5H) 9.58 (s, 1H)

EXAMPLE 2

(a) (2R,3S)-3-(N-benzoyl)-amino-4-phenyl-1,2-butanediol 50 g of ethyl (2R,3S)-3-(N-benzoyl)-amino-4-phenyl-2-hydroxybutyrate was dissolved in 400 ml of ethanol. The resulting solution was cooled to 0° C. 23.11 g of sodium borohydride was added to the cooled solution under stirring. The reaction was effected while gradually elevating the temperature of the resulting mixture up to room temperature. After the completion of the reaction, the reaction mixture was neutralized with 3N HCl to adjust the pH thereof to 5, followed by distilling off the solvent under reduced pressure. Water and ethyl acetate were added to the resulting concentrate to effect extraction. The ethyl acetate layer was washed with an aqueous saturated solution of sodium chloride, dried over magnesium sulfate, and filtered. The filtrate was concentrated, and the concentrate was purified by recrystallization to obtain 37.5 g of (2R,3S)-3-(N-benzoyl)-amino-4-phenyl-1,2-butanediol in a yield of 97%.

1H-NMR (CDCl$_3$, D$_2$O)

δ(ppm) 3.05 (d, 2H, J=7.78 Hz) 3.40–3.61 (m, 2H) 3.75–3.86 ( m, 1H ) 4.38–4.53 ( m, 1H ) 6.46–6.63 (br, 1H) 7.13–7.52 (m, 8H) 7.58–7.69 (m, 2H)

Optical rotation [α]20D = −100.14 (cl.003, MeOH)

Melting point: 105.5°–106.5° C.

Here, ethyl (2R,3S)-3-(N-benzoyl)-amino-4-phenyl-2-hydroxybutyrate as the starting material can be obtained according to a process disclosed in Japanese Patent Publication No. 21,466/1986. Specifically, (threo)-(2RS)-3-benzoylamino-2-hydroxy-4-phenylbutyric acid is reacted with R(+)-1-phenylethylamine in ethanol, followed by precipitation of the (2R,3S) isomer of the R(+)-1-phenylethylamine salt thereof, which is then treated with an acid such as sulfuric acid to obtain free (2R,3S)-3-(N-benzoyl)-amino-4-phenyl-2-hydroxybutyric acid, which is reacted with ethanol according to a customary method to obtain the ethyl ester thereof.

(b) 2S-(N-benzoyl)-phenylalaninal 37.5 g of (2R,3S)-3-(N-benzoyl)-amino-4-phenyl-1,2-butanediol was added to a solvent mixture composed of 160 ml of methylene chloride and 80 ml of water. The resulting mixture was cooled to 0° C. 48.8 g of sodium periodate was added to the cooled mixture under stirring to effect the reaction for 2 hours. After the completion of the reaction, water was added to the reaction mixture to dissolve therein inorganic salts, followed by extraction with methylene chloride. The methylene chloride layer was washed with water and an aqueous saturated solution of sodium chloride, dried over magnesium sulfate, and filtered. The filtrate was concentrated, and the concentrate was purified by recrystallization to quantitatively obtain 32.3 g of 2S-(N-benzoyl)-phenylalaninal.

1H-NMR (CDCl$_3$)

δ(ppm) 3.25–3.34 (m, 2H) 4.92 (q, 1H, J=6.5 Hz) 6.68–6.81 (br, 1H) 7.13–7.78 (m, 10H) 9.72 (s, 1H)

Optical rotation [α]20D = −111.31 (cl.004, MeOH)

Melting point: 133.0°–134.0° C.

According to the present invention, a high-purity optically active 2-aminopropanal can be obtained in a high yield from the corresponding stable 3-amino-1,2-butanediol through oxidative cleavage thereof under such neutral and mild conditions that the configuration of the amino group thereof subject to epimerization can be maintained as such in the resulting product.

What is claimed is:

1. A process for preparing an optically active 2-aminopropanal represented by the following formula (1):

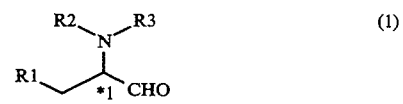

wherein R1 is a hydrocarbon group having 3 to 6 carbon atoms; R2 is a hydrogen atom or an N-protecting group, R3 is a hydrogen atom or an N-protecting group, or R2 and R3 together represent an N-protecting group; and the configuration at the *1 position is S or R:

comprising oxidative cleavage of an optically active 3-amino-1,2-butanediol represented by the following formula (2):

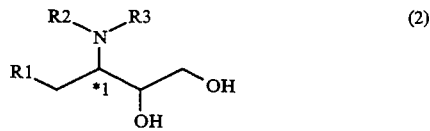

wherein R1, R2, R3 and the configuration at the position *1 are each as defined above.

2. A process for preparing an optically active 2-aminopropanal as claimed in claim 1, wherein R2 in the compound of the formula (2) is a hydrogen atom or a group selected from the group consisting of acyl protecting groups, urethane-forming protecting groups, and a phthalyl group, R3 in the compound of the formula (2) is a hydrogen atom or a group selected from the group consisting of acyl protecting groups, urethane-forming protecting groups, and a phthalyl group, or R2 and R3 in the compound of the formula (2) together represent a group selected from the group consisting of acyl protecting groups, urethane-forming protecting groups, and a phthalyl group.

3. A process for preparing an optically active 2-aminopropanal as claimed in claim 1, wherein said N-protecting group for R2 and/or R3 in the compound of the formula (2) are each a group selected from the group consisting of a benzyloxycarbonyl group and alkoxycarbonyl groups with the alkoxy group having 1 to 6 carbon atoms.

4. A process for preparing an optically active 2-aminopropanal as claimed in claim 1, wherein R1 in the compound of the formula (2) is a cyclic hydrocarbon group having 6 carbon atoms.

5. A process for preparing an optically active 2-aminopropanal as claimed in claim 1, wherein R1 in the compound of the formula (2) is a cyclohexyl group.

6. A process for preparing an optically active 2-aminopropanal as claimed in claim 1, wherein said oxidative cleavage of the compound of the formula (2) is carried out using a periodic acid compound.

7. A process for preparing an optically active 2-aminopropanal represented by the following formula (1):

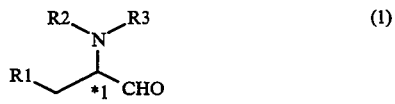

wherein R1 is a hydrocarbon group having 3 to 6 carbon atoms; R2 is a hydrogen atom or an N-protecting group, R3 is a hydrogen atom or an N-protecting group, or R2 and R3 together represent an N-protecting group; and the configuration at the *1 position is S or R:

comprising reduction of an optically active 3-amino-2-hydroxybutyric acid or ester represented by the following formula (3):

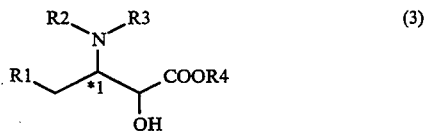

wherein R1, R2, R3, and the configuration at the position *1 are each as defined above; and R4 is a hydrogen atom or an ester residue; and oxidative cleavage of the resulting optically active 3-amino-1,2-butanediol represented by the following formula (2):

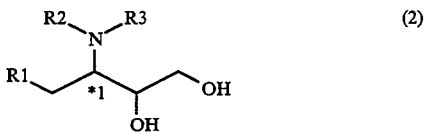

wherein R1, R2, R3 and the configuration at the position *1 are each as defined above.

8. A process for preparing an optically active 2-aminopropanal as claimed in claim 7, wherein R4 in the compound of the formula (3) is an alkyl group having 1 to 4 carbon atoms or an aryl group.

9. A process for preparing an optically active 2-aminopropanal as claimed in claim 7, wherein in the compound of the formula (3), R1 is a cyclohexyl group, one of R2 and R3 is a hydrogen atom and the other is a benzyloxycarbonyl group, and R4 is an alkyl group having 1 to 4 carbon atoms.

10. A process for preparing an optically active 2-aminopropanal as claimed in claim 7, wherein R4 is an ester residue, and wherein said reduction of the compound of the formula (3) is carried out using a boron hydride compound, while said oxidative cleavage of the compound of the formula (2) is carried out using a periodic acid compound.

* * * * *